United States Patent
Yang et al.

(10) Patent No.: US 10,324,227 B2
(45) Date of Patent: Jun. 18, 2019

(54) SYSTEM AND METHOD FOR DETERMINING THE ADIABATIC STRESS DERIVATIVE OF THE TEMPERATURE FOR ROCKS UNDER WATER

(71) Applicant: SOUTH CHINA SEA INSTITUTE OF OCEANOLOGY, CHINESE ACADEMY OF SCIENCES, Guangzhou, Guangdong (CN)

(72) Inventors: Xiaoqiu Yang, Guangzhou (CN); Weiren Lin, Kyoto (JP); Ziying Xu, Guangzhou (CN); Xiaobin Shi, Guangzhou (CN); Hehua Xu, Guangzhou (CN)

(73) Assignee: SOUTH CHINA SEA INSTITUTE OF OCEANOLOGY, CHINESE AC, Guangzhou (CN)

( * ) Notice: Subject to any disclaimer, the term of this patent is extended or adjusted under 35 U.S.C. 154(b) by 102 days.

(21) Appl. No.: 15/546,743

(22) PCT Filed: Apr. 19, 2016

(86) PCT No.: PCT/CN2016/079685
§ 371 (c)(1),
(2) Date: Jul. 27, 2017

(87) PCT Pub. No.: WO2017/152471
PCT Pub. Date: Sep. 14, 2017

(65) Prior Publication Data
US 2018/0120476 A1    May 3, 2018

(30) Foreign Application Priority Data
Mar. 8, 2016 (CN) .......................... 2016 1 0130626

(51) Int. Cl.
*G06F 11/30* (2006.01)
*G01V 9/00* (2006.01)
(Continued)

(52) U.S. Cl.
CPC ............... *G01V 9/005* (2013.01); *G01N 3/08* (2013.01); *G01N 7/00* (2013.01); *G01N 25/20* (2013.01);
(Continued)

(58) Field of Classification Search
CPC ..................................................... G01V 5/009
See application file for complete search history.

(56) References Cited

U.S. PATENT DOCUMENTS

2002/0046569 A1* 4/2002 Faqih .................... B01D 5/009
62/188

FOREIGN PATENT DOCUMENTS

CN  101949803      *  1/2011
CN  101949803 A        1/2011
(Continued)

OTHER PUBLICATIONS

Deng et al., "The Study on the Variation of Thermal State of Rocks Caused by the Variation of Stress State of Rocks," Earthquake Research in China, vol. 13, No. 2, Jun. 1997, pp. 179-185, cited in ISR (8 pages, including English abstract).
(Continued)

*Primary Examiner* — Phuong Huynh
(74) *Attorney, Agent, or Firm* — Westerman, Hattori, Daniels & Adrian, LLP

(57) ABSTRACT

A system and method for determining adiabatic stress derivative of temperature for rocks under water. The system includes three pressure vessels disposed in seawater. A data collecting unit is in the first pressure vessel. A rock sample is in a first chamber of the second pressure vessel. A
(Continued)

temperature sensor is in each of the center of the rock, the surface of the rock sample, and the first chamber. A pressure sensor is also in the first chamber. Outputs of the temperature sensors and the pressure sensor are communicated with inputs of the data collecting unit. A first drain valve is provided on the second pressure vessel and communicated with the first chamber. A second drain valve is provided between the second pressure vessel and the third pressure vessel, and communicated with the first chamber and the second chamber.

6 Claims, 2 Drawing Sheets

(51) Int. Cl.
*G01N 25/20* (2006.01)
*G01N 3/08* (2006.01)
*G01N 7/00* (2006.01)
*G01N 33/24* (2006.01)

(52) U.S. Cl.
CPC ..... *G01N 33/24* (2013.01); *G01N 2203/0224* (2013.01); *G01N 2203/0232* (2013.01); *G01N 2203/0242* (2013.01); *G01N 2203/0676* (2013.01); *G01N 2203/0694* (2013.01)

(56) References Cited

FOREIGN PATENT DOCUMENTS

| | | |
|---|---|---|
| CN | 102053253 A | 5/2011 |
| CN | 102175712 A | 9/2011 |
| CN | 104749210 A | 7/2015 |
| CN | 105067450 A | 11/2015 |
| CN | 105259036 A | 1/2016 |
| EP | 1001266 A1 | 5/2000 |
| JP | 8-247978 A | 9/1996 |

OTHER PUBLICATIONS

International Search Report dated Dec. 14, 2016, issued in counterpart International Application No. PCT/CN2016/079685 (8 pages, including English translation).

\* cited by examiner

SYSTEM AND METHOD FOR DETERMINING THE ADIABATIC STRESS DERIVATIVE OF THE TEMPERATURE FOR ROCKS UNDER WATER

TECHNICAL FIELD

The present invention is directed to a system and a method for determining the adiabatic stress derivative of the temperature for rocks under water, and falls within the realm of determination of thermoelastic parameters of rocks.

BACKGROUND OF THE INVENTION

Usually, the stress state of the crust can be caused by various geological processes, e.g., mantle convection, plate motions, volcanic eruptions and earthquakes. And it will induce temperature change in the earth's interior, especially in the crust. Based on thermos-elasticity theory, a convenient relationship between the temperature change ($\Delta T$) and the sum of the change of the principle stresses ($\Delta \sigma$) can be described by the following equation:

$$\Delta T = \frac{-\alpha}{\rho c_p} \cdot T_0 \cdot \Delta \sigma, \qquad (1)$$

where, $T_0$ is the thermodynamic temperature; $\rho c_p$ is the volumetric heat capacity at constant pressure; $\alpha$ is the coefficient of linear thermal expansion; $\Delta \sigma$ denotes the change of the sum of the three principal stresses.

The magnitude of the temperature change in response to the stress change varies in different kinds of rock. Therefore, to determine the adiabatic stress derivative of the temperature ($\Delta T/\Delta \sigma$) for different rocks, will help to understand the mechanism of temperature change of the earth's interior, and provide the theoretical basis for stress and temperature monitoring and earthquake prevention in active tectonic zones.

In the existing methods for determining the adiabatic stress derivative of the temperature, temperature sensors are usually attached to the surface of the rock samples and in contact with the air, such that the system is open to the external environment, and it is impossible to achieve instant loading and unloading due to the restriction of stress loading units. Thus, it is impossible to achieve stress loading and unloading under adiabatic condition and thereby the results of such determination will be affected significantly by the heat exchange between the rock sample and the air.

Deep sea, with a very high pressure, is a natural "high pressure pump". On the other hand, within a time scale of 1-3 hours, deep sea water has very little fluctuation in temperature, which makes it an ideal thermostatic environment.

SUMMARY OF THE INVENTION

In order to overcome the prior art deficiencies, the objective of the present invention is to provide a system for determining the adiabatic stress derivative of the temperature for rocks under water, which allows rapid loading and unloading by instantaneously opening a drain valve of the second pressure vessel. Within 10-20 seconds after the rapid loading (or unloading), the temperature in the center of rock sample is not yet affected by the external temperature change, such that the adiabatic condition in the center of the rock sample is achieved during rapid loading (or unloading) process. And thereby we can obtain the adiabatic stress derivative of the temperature ($\Delta T/\Delta \sigma$) of the rock, namely the change in temperature per unit stress change, by real-time monitoring the change in confining pressure in the pressure vessel and temperature in the center of the rock sample.

The system of the present invention, for determining the adiabatic stress derivative of the temperature for rocks under water, comprises three pressure vessels disposed in seawater, wherein, a data collecting unit is disposed in a first pressure vessel, a rock sample is disposed in a first chamber of a second pressure vessel, and a second chamber is provided in a third pressure vessel; the first chamber is filled with seawater, and the second chamber is filled with air; a first temperature sensor is disposed in a center of the rock sample, a second temperature sensor is disposed on a surface of the rock sample, and a third temperature sensor and a pressure sensor are disposed in the seawater in the first chamber; outputs of the first temperature sensor, the second temperature sensor, the third temperature sensor and the pressure sensor are communicated with inputs of the data collecting unit; a first drain valve is provided on the second pressure vessel and communicated with the first chamber; a second drain valve is provided between the second pressure vessel and the third pressure vessel, and communicated with the first chamber and the second chamber.

The surface of the rock sample is provided with a rubber jacket that is configured to encapsulate the rock sample.

Another objective of the present invention is to provide a method for determining the adiabatic stress derivative of the temperature for rocks under water, which allows rapid loading and unloading of a rock sample by instantaneously opening a drain valve of the second pressure vessel. Within 10-20 seconds after the rapid loading (or unloading), the temperature in the center of rock sample is not yet affected by the external temperature change, such that the adiabatic condition in the rock sample center is achieved during rapid loading (or unloading) process. And thereby we can obtain the adiabatic stress derivative of the temperature ($\Delta T/\Delta \sigma$) of the rock, namely the change in temperature per unit stress change, by real-time monitoring the change in confining pressure in the pressure vessel and temperature in the center of the rock sample.

The method of the present invention, for determining the adiabatic stress derivative of the temperature for rocks under water, comprises the following steps:

step 1: disposing a first temperature sensor in a center of a rock sample having a cylindrical shape, disposing a second temperature sensor on a surface of the rock sample, and watertightly encapsulating the rock sample with a rubber jacket so as to obtain a rock sample assembly;

step 2: disposing the rock sample assembly, a third temperature sensor and a pressure sensor in a first chamber of a second pressure vessel, the first chamber being filled with seawater;

step 3: electrically connecting the first temperature sensor, the second temperature sensor, the third temperature sensor and the pressure sensor, to a data collecting unit disposed in a first pressure vessel, with a watertight cable; disposing a first drain valve and a second drain valve on the second pressure vessel, the first drain valve being communicated with the first chamber, and both ends of the second drain valve being respectively communicated with the first chamber and a second chamber of a third pressure vessel, to form a whole system for determining the adiabatic stress derivative of the temperature; turning on a temperature and pressure collecting module of the data collecting unit so as to monitor temperature and confining pressure;

step 4, rapid loading: delivering the whole system to a predetermined ocean depth by an underwater vehicle; when temperature of the whole system reaches equilibrium, collecting a first temperature by the first temperature sensor, and collecting a first confining pressure by the pressure sensor; then rapidly opening the first drain valve by a mechanical arm of the underwater vehicle or an underwater motor so that the confining pressure in the second vessel rises instantaneously to the seawater pressure; collecting a second confining pressure by the pressure sensor, and collecting a second temperature by the first temperature sensor;

step 5, rapid unloading: when temperature of the whole system reaches equilibrium again, collecting a third temperature by the first temperature sensor; by the mechanical arm, closing the first drain valve and then rapidly opening the second drain valve so that the confining pressure in the second vessel decreases instantaneously; collecting a third confining pressure by the pressure sensor, and collecting a fourth temperature by the first temperature sensor; and step 6: obtaining a temperature difference $\Delta T_1$ and a confining pressure difference $\Delta \sigma_1$ by the first temperature, the second temperature, the first confining pressure and the second confining pressure which are obtained in step 4, and thereby a adiabatic stress derivative of the temperature $\Delta T_1/\Delta \sigma_1$ of the rock during rapid loading process under water is determined; obtaining a temperature difference $\Delta T_2$ and a confining pressure difference $\Delta \sigma_2$ by the third temperature, the fourth temperature, the second confining pressure and the third confining pressure which are obtained in step 4 and step 5, and thereby a adiabatic stress derivative of the temperature $\Delta T_2/\Delta \sigma_2$ of the rock during rapid unloading process under water is determined too.

Temperature of the whole system reaches equilibrium when each temperature collected by the three temperature sensors becomes steady.

Each of the second temperature, the fourth temperature, the second confining pressure and the third confining pressure is collected within 10-20 seconds after the corresponding drain valve is opened.

The temperature difference $\Delta T_1$ equals to the second temperature minus the first temperature, and the confining pressure difference $\Delta \sigma_1$ equals to the second confining pressure minus the first confining pressure; the temperature difference $\Delta T_2$ equals to the fourth temperature minus the third temperature, and the confining pressure difference $\Delta \sigma_2$ equals to the third confining pressure minus the second confining pressure.

In the system and the method provided by the present invention, the center and the surface of a cylindrical rock sample are respectively provided with a temperature sensor. The rock sample is encapsulated with a rubber jacket and disposed in a pressure vessel which is filled with seawater, and then the system is delivered to a predetermined ocean depth by an underwater vehicle. Instant loading (or unloading) for the rock sample is achieved by rapidly opening the drain valves by the underwater vehicle. The system and the method have the following advantages.

1) Deep sea, with a very high pressure, is a natural "high pressure pump", and thus the present system can work without stress loading units or pressure pumps.

2) Within a time scale of 1-3 hours, deep sea water has very little fluctuation in temperature, which makes it an ideal thermostatic environment. Within 10-20 seconds after the rapidly opening the drain valves, the temperature in the centers of rock samples are not yet affected by the temperature change of the seawater in the pressure vessel, such that the adiabatic condition in the rock sample center is achieved during rapid loading (or unloading) process. And thereby we can obtain the adiabatic stress derivative of the temperature ($\Delta T/\Delta \sigma$) of the rock, by real-time monitoring the changes of confining pressure in the pressure vessel and temperature in the rock sample center.

Figure 1:
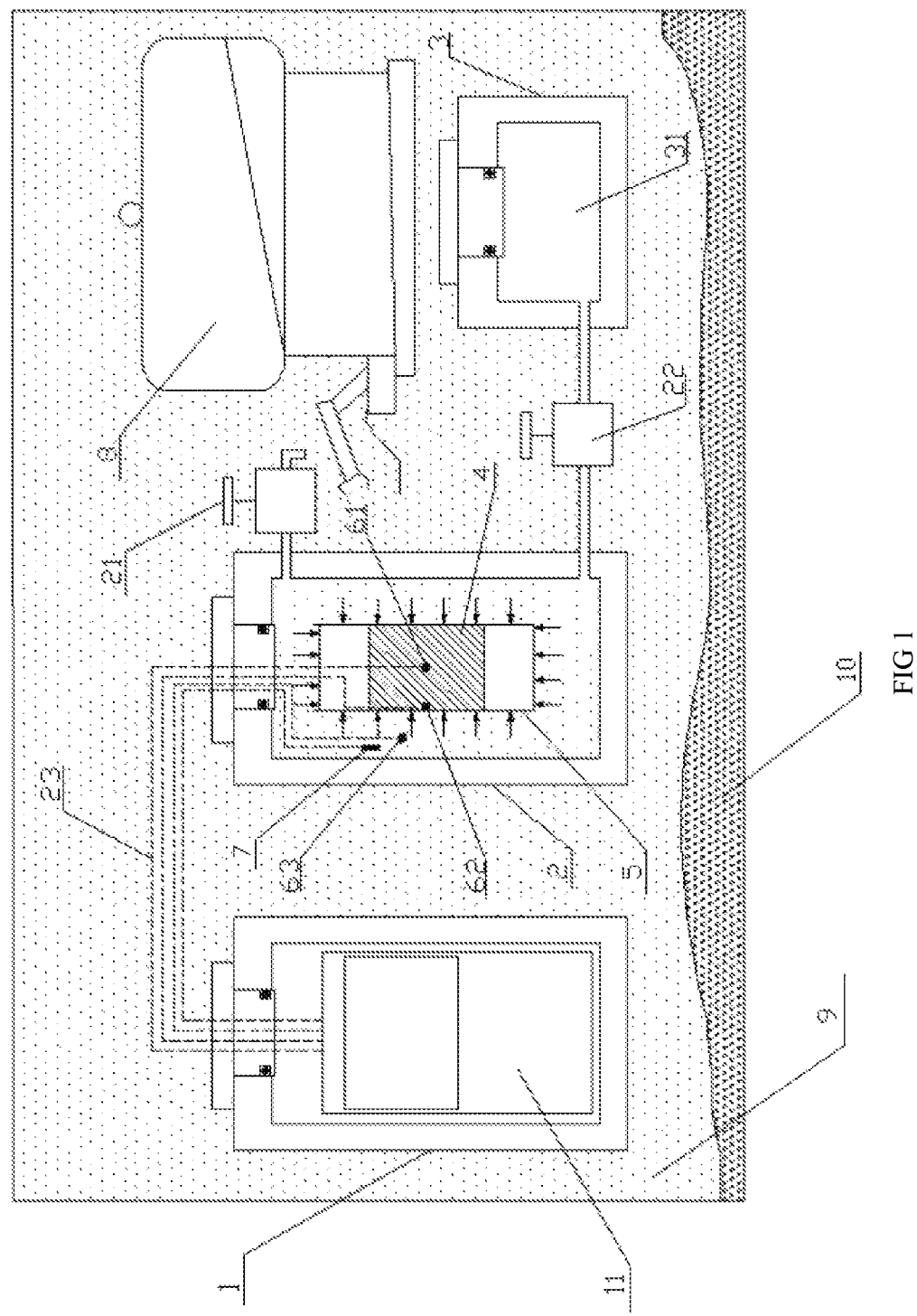
FIG. 1 is a schematic diagram of the system for determining the adiabatic stress derivative of the temperature for rocks under water.

Reference characters in the drawings: 1: first pressure vessel; 11: data collecting unit; 2: second pressure vessel; 21: first drain valve; 22: second drain valve; 23: watertight cable; 3: third pressure vessel; 31: chamber; 4: rock sample; 5: rubber jacket; 61: temperature sensor; 62: second temperature sensor; 63: third temperature sensor; 7: pressure sensor; 8: underwater vehicle; 9: seawater; 10: seafloor.

DETAILED DESCRIPTION OF PREFERRED EMBODIMENT

Further characteristics and advantages of the present invention will be more readily apparent from the below detailed description of the drawings and the embodiment.

Embodiment

As shown in FIG. 1, provided is a system for determining the adiabatic stress derivative of the temperature for rocks, comprising three pressure vessels, a first pressure vessel 1, a second pressure vessel 2 and a third pressure vessel 3. A data collecting unit 11 is disposed in the first pressure vessel 1. A cylindrical rock sample assembly is disposed in a first chamber of the second pressure vessel. The cylindrical rock sample assembly includes a rock sample 4 having a cylindrical shape, a first temperature sensor 61 disposed in the center of the rock sample 4, and a second temperature sensor 62 disposed on the surface of the rock sample 4, and then they are encapsulated with a rubber jacket 5 and disposed in the second pressure vessel 2 having a first chamber (filled with seawater initially). Further disposed in the first chamber (but outside the rock sample 4) of the second pressure vessel 2 are a third temperature sensor 63 and a pressure sensor 7, which are configured to monitor the temperature and confining pressure in the second pressure vessel 2. A second chamber 31 is provided in the third pressure vessel 3 (filled with air initially). Between the first pressure vessel 1 and the second pressure vessel 2, the three temperature sensors 6 and the pressure sensor 7 are connected to the data collecting unit 11 with watertight cable 23. The second pressure vessel 2 is provided with a first drain valve 21. The second pressure vessel 2 is connected to the third pressure vessel 3 with a stainless steel pipe, and the stainless steel pipe is provided with a second drain valve 22.

The system, for determining the adiabatic stress derivative of the temperature for rocks under water, is operated as follows.

Step 1: Disposing the first temperature sensor 61 in the center of the rock sample 4 having a cylindrical shape, disposing the second temperature sensor 62 on the surface of the rock sample, and watertightly encapsulating the rock sample 4 with a rubber jacket 5 so as to obtain a cylindrical rock sample assembly.

Step 2: Disposing the rock sample assembly, the pressure sensor 7 and the third temperature sensor 63 in the second pressure vessel 2. Sealing the second pressure vessel 2 after it is filled with seawater. Then electrically connecting all the temperature sensors and the pressure sensor 7 to the data collecting unit 11 in the first pressure vessel 1 with the watertight cable 23, as shown in FIG. 1. Connecting the second pressure vessel 2 to the third pressure vessel 3 with the stainless steel pipe as shown in FIG. 1. Turning on a temperature and pressure collecting module of the data collecting unit so as to monitor the temperature and confining pressure.

Step 3: Delivering the whole system for determining the adiabatic stress derivative of the temperature to a predetermined depth in seawater 9 by an underwater vehicle 8. The depth can be 6,000 meters for example, having a pressure of 60 MPa. As shown in FIG. 1, the bottom of the seawater 9 is a seafloor 10. When temperature of the whole system reaches equilibrium, rapidly opening the first drain valve 21 by a mechanical arm of the underwater vehicle 8 (or, certainly, an underwater motor) so that the confining pressure in the second vessel 2 rises instantaneously to the seawater pressure (for example, 60 MPa) within 1-2 seconds.

Step 4: When temperature of the whole system reaches equilibrium again, by the mechanical arm, closing the first drain valve 21 and then rapidly opening the second drain valve 22 between the second pressure vessel 2 and the third pressure vessel 3, so that the confining pressure in the second vessel 2 decreases instantaneously within 1-2 seconds.

After the above operation, the rock sample 4 is subject to a rapid loading and a rapid unloading, and during the process the temperature and the confining pressure are real-time monitored and recorded. Within 10-20 seconds after the rapidly opening the drain valves, since the temperature in the center of the rock sample is not yet affected by the temperature change of the seawater in the second pressure vessel 2, such that the adiabatic condition in the rock sample center is achieved during rapid loading (or unloading) process. As such, we can obtain the adiabatic stress derivative of the temperature ($\Delta T/\Delta \sigma$) by real-time collecting and analyzing the changes of confining pressure in the pressure vessel and temperature in the rock sample center.

Figure 2:
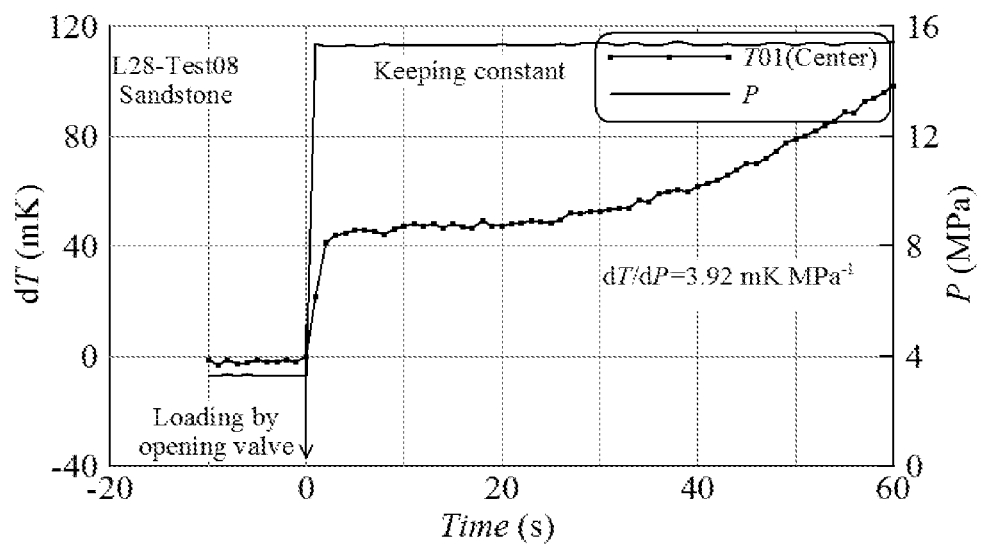
FIG. 2 shows the temperature response curve of a sandstone sample during a rapid loading process. The sample was collected from the Longmenshan Fault.
Figure 3:
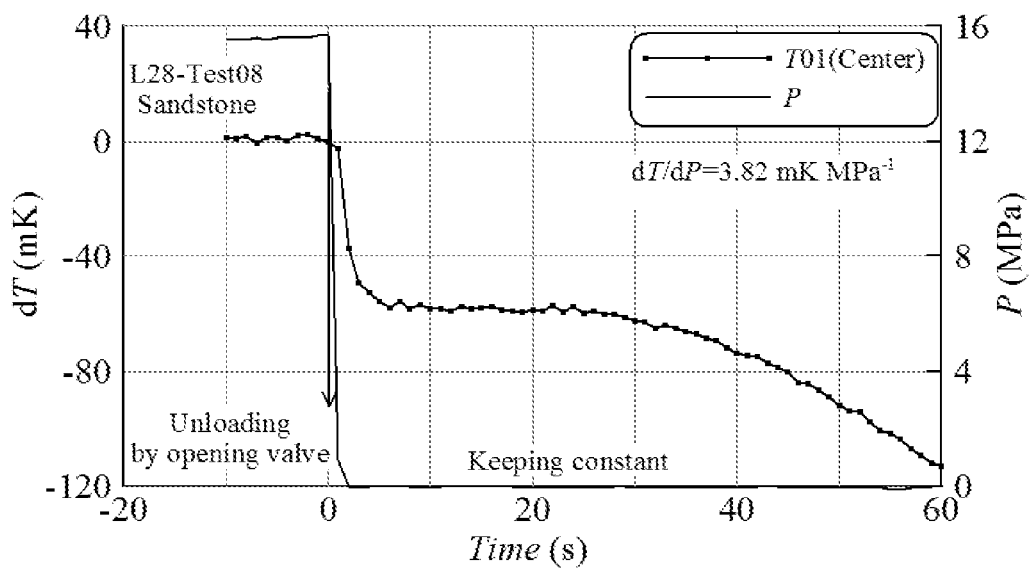
FIG. 3 shows the temperature response curve of a sandstone sample during a rapid unloading process. The sample was collected from the Longmenshan Fault.

The inventors had performed a test using a system practically consistent with that of the present invention, but different in that they introduced a high pressure pump to raise the confining pressure in a large pressure vessel (configured to simulate a deep sea environment having high pressure, for example, 130 MPa). As such, the confining pressure in the pressure vessel containing the rock sample assembly rose instantaneously once the drain valve is open. FIGS. 2 and 3 show the temperature response curves during a rapid loading process (FIG. 2) and a rapid unloading process (FIG. 3) on a sandstone sample (L28) which was collected from the Longmenshan Fault Zone. After the rapid loading (or unloading), an instant temperature increase (or decrease) in the center of the rock sample was observed. Then the temperature kept constant for about 20 seconds. After that, the temperature in the rock sample center increased (or decreased) gradually as affected by the temperature change of seawater. Results ($\Delta T/\Delta \sigma$) of rock sample L28 are 3.92 mK/MPa and 3.82 mK/MPa during rapid loading and unloading processes, respectively. The relative error is within 3%. The inventors had performed the tests on 15 different rock samples from different areas, and they obtained the good results of all tests.

The results showed that, the method and the system of the present invention were suitable for determining the adiabatic stress derivative of the temperature for rocks.

The above detailed description is a specific explanation for feasible embodiments of the present invention. The embodiments are not used for limiting the scope of the present invention. Any equivalent or changes made on the basis of the present invention shall fall within the scope of the present invention.

The invention claimed is:

1. A system for determining an adiabatic stress derivative of the temperature for rocks under water, comprising:
    a first pressure vessel including a data collecting unit;
    a second pressure vessel including a first chamber accommodating a rock sample, the first chamber being filled with seawater;
    a third pressure vessel including a second chamber that is filled with air, wherein the first pressure vessel, the second pressure vessel, and the third pressure vessel are disposed in seawater;
    a first temperature sensor disposed in a center of the rock sample;
    a second temperature sensor disposed on a surface of the rock sample;
    a third temperature sensor disposed in the seawater in the first chamber;
    a pressure sensor disposed in the seawater in the first chamber, wherein outputs of the first temperature sensor, the second temperature sensor, the third temperature sensor and the pressure sensor are input into the data collecting unit;
    a first drain valve provided on the second pressure vessel, the first drain valve being in communication with the first chamber; and
    a second drain valve provided between the second pressure vessel and the third pressure vessel, the second drain valve being in communication with the first chamber and the second chamber.

2. The system according to claim 1, wherein the surface of the rock sample is provided with a rubber jacket that is configured to encapsulate the rock sample.

3. A method for determining an adiabatic stress derivative of the temperature for rocks under water, comprising the steps of:
    disposing a first temperature sensor in a center of a rock sample having a cylindrical shape;
    disposing a second temperature sensor on a surface of the rock sample, and watertightly encapsulating the rock sample with a rubber jacket so as to obtain a rock sample assembly;
    disposing the rock sample assembly, a third temperature sensor and a pressure sensor in a first chamber of a second pressure vessel, the first chamber being filled with seawater;
    electrically connecting, with a watertight cable, the first temperature sensor, the second temperature sensor, the third temperature sensor, and the pressure sensor to a data collecting unit disposed in a first pressure vessel;
    disposing a first drain valve and a second drain valve on the second pressure vessel, the first drain valve being in communication with the first chamber, and both ends of the second drain valve being respectively in communication with the first chamber and a second chamber of a third pressure vessel, to form a whole system for determining the adiabatic stress derivative of the temperature for rocks under water;
turning on a temperature and pressure collecting module of the data collecting unit so as to monitor temperature and confining pressure;
performing a rapid loading process, the rapid loading process including:
   delivering the whole system to a predetermined ocean depth by an underwater vehicle;
   when a temperature of the whole system reaches equilibrium, collecting a first temperature by the first temperature sensor, and collecting a first confining pressure by the pressure sensor;
   rapidly opening the first drain valve by a mechanical arm of the underwater vehicle or an underwater motor so that the confining pressure in the second vessel rises to a seawater pressure;
   collecting a second confining pressure by the pressure sensor; and
   collecting a second temperature by the first temperature sensor;
performing a rapid unloading process, the rapid unloading process including:
   when the temperature of the whole system reaches equilibrium again after the rapid loading process, collecting a third temperature by the first temperature sensor;
   by the mechanical arm, closing the first drain valve and then rapidly opening the second drain valve so that the confining pressure in the second vessel decreases;
   collecting a third confining pressure by the pressure sensor; and
   collecting a fourth temperature by the first temperature sensor;
obtaining a temperature difference $\Delta T_1$ and a confining pressure difference $\Delta \sigma_1$ by the first temperature, the second temperature, the first confining pressure and the second confining pressure, and thereby a adiabatic stress derivative of the temperature $\Delta T_1/\Delta \sigma_1$ of the rock during the rapid loading process under water is determined; and
obtaining a temperature difference $\Delta T_2$ and a confining pressure difference $\Delta \sigma_2$ by the third temperature, the fourth temperature, the second confining pressure and the third confining pressure, and thereby, the adiabatic stress derivative of the temperature $\Delta T_2/\Delta \sigma_2$ of the rock during rapid unloading under water is determined.

4. The method according to claim 3, wherein, the temperature of the whole system reaches equilibrium in the rapid loading process and in the rapid unloading process when temperatures collected by each of the first temperature sensor, the second temperature sensor, and the third temperature sensor becomes steady.

5. The method according to claim 3, wherein, each of the second temperature, the fourth temperature, the second confining pressure and the third confining pressure is collected within 10-20 seconds after the corresponding drain valve is opened.

6. The method according to claim 3, wherein the temperature difference $\Delta T_1$ is the second temperature minus the first temperature, the confining pressure difference $\Delta \sigma_1$ is the second confining pressure minus the first confining pressure, the temperature difference $\Delta T_2$ is the fourth temperature minus the third temperature, and the confining pressure difference $\Delta \sigma_2$ is the third confining pressure minus the second confining pressure.

* * * * *

UNITED STATES PATENT AND TRADEMARK OFFICE
CERTIFICATE OF CORRECTION

PATENT NO. : 10,324,227 B2
APPLICATION NO. : 15/546743
DATED : June 18, 2019
INVENTOR(S) : Xiaoqiu Yang et al.

Page 1 of 1

It is certified that error appears in the above-identified patent and that said Letters Patent is hereby corrected as shown below:

On the Title Page

Item (73):
Change:
(73) Assignees: SOUTH CHINA SEA INSTITUTE OF OCEANOLOGY, CHINESE AC,
　　　　　　　　Guangzhou (CN)

To be:
(73) Assignees: SOUTH CHINA SEA INSTITUTE OF OCEANOLOGY, CHINESE ACADEMY
　　　　　　　　OF SCIENCES, Guangzhou (CN)

Signed and Sealed this
Sixth Day of August, 2019

Andrei Iancu
*Director of the United States Patent and Trademark Office*